(12) United States Patent
Ellingson et al.

(10) Patent No.: US 9,919,158 B2
(45) Date of Patent: Mar. 20, 2018

(54) CONFIGURING OPERATING PARAMETERS OF A MEDICAL DEVICE BASED ON EXPOSURE TO A DISRUPTIVE ENERGY FIELD

(75) Inventors: Michael L. Ellingson, St. Louis Park, MN (US); Hyun J. Yoon, Vadnais Heights, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 613 days.

(21) Appl. No.: 12/648,690

(22) Filed: Dec. 29, 2009

(65) Prior Publication Data
US 2011/0160791 A1 Jun. 30, 2011

(51) Int. Cl.
*A61N 1/00* (2006.01)
*A61N 1/37* (2006.01)
*A61N 1/368* (2006.01)

(52) U.S. Cl.
CPC .......... *A61N 1/3718* (2013.01); *A61N 1/3688* (2013.01); *A61N 1/37* (2013.01)

(58) Field of Classification Search
CPC ....... A61N 1/3688; A61N 1/37; A61N 1/3718
USPC ................................................ 607/9, 27, 28
See application file for complete search history.

(56) References Cited

U.S. PATENT DOCUMENTS

| | | |
|---|---|---|
| 3,688,776 A | 9/1972 | Kenny |
| 4,091,818 A * | 5/1978 | Brownlee et al. ............ 607/9 |
| 4,301,804 A | 11/1981 | Thompson et al. |
| 4,386,610 A | 7/1983 | Leckrone |
| 4,541,431 A | 9/1985 | Ibrahim |
| 4,941,471 A | 7/1990 | Mehra |
| 5,170,806 A | 12/1992 | Colen |
| 5,197,468 A | 3/1993 | Proctor et al. |
| 5,209,233 A | 5/1993 | Holland et al. |
| 5,217,010 A | 6/1993 | Tsitlik et al. |
| 5,438,990 A | 8/1995 | Wahlstrand |
| 5,545,185 A | 8/1996 | Denker |
| 5,629,622 A | 5/1997 | Sampini |

(Continued)

FOREIGN PATENT DOCUMENTS

| | | |
|---|---|---|
| EP | 0713714 | 5/1996 |
| EP | 0931566 | 7/1999 |

(Continued)

OTHER PUBLICATIONS

P0037148.01 (PCT/US2010/058194) PCT Notification of Transmittal of the International Search Report and the Written Opinion of the International Searching Authority, 10 pages.

(Continued)

*Primary Examiner* — Lindsey G Wehrheim

(57) ABSTRACT

An implantable medical device (IMD) determines an effect of the disruptive energy field and adjusts one or more operating parameters of the IMD based on at least the determined effect. In some instances, the IMD may determine an actual effect of the disruptive energy field, such as a temperature change, impedance change, pacing or sensing threshold change, MRI-induced interference one pacing or sensing, or other actual effect. In other instances, the IMD may determine a predicted effect of the disruptive energy field based on one or more characteristics of the exposure. In any case, the IMD adjusts one or more parameters based on at least the determined effect.

38 Claims, 8 Drawing Sheets

(56) References Cited

U.S. PATENT DOCUMENTS

| | | | |
|---|---|---|---|
| 5,647,379 A * | 7/1997 | Meltzer | A61N 1/37 128/897 |
| 5,649,965 A | 7/1997 | Pons et al. | |
| 5,662,694 A | 9/1997 | Lidman et al. | |
| 5,697,958 A | 12/1997 | Paul et al. | |
| 5,722,998 A | 3/1998 | Prutchi et al. | |
| 5,814,085 A | 9/1998 | Hill | |
| 5,817,136 A | 10/1998 | Nappholz et al. | |
| 5,978,710 A | 11/1999 | Prutchi et al. | |
| 6,101,417 A | 8/2000 | Vogel et al. | |
| 6,188,926 B1 | 2/2001 | Vock | |
| 6,209,764 B1 | 3/2001 | Hartlaub et al. | |
| 6,850,805 B2 | 2/2005 | Connelly et al. | |
| 6,937,906 B2 | 8/2005 | Terry et al. | |
| 7,082,328 B2 | 7/2006 | Funke | |
| 7,164,950 B2 | 1/2007 | Kroll et al. | |
| 7,212,863 B2 | 5/2007 | Strandberg | |
| 7,369,898 B1 | 5/2008 | Kroll et al. | |
| 2002/0026224 A1 * | 2/2002 | Thompson et al. | 607/60 |
| 2003/0083570 A1 | 5/2003 | Cho et al. | |
| 2003/0140931 A1 | 7/2003 | Zeijlemaker et al. | |
| 2003/0144705 A1 | 7/2003 | Funke | |
| 2004/0162591 A1 * | 8/2004 | Jorgenson | A61N 1/3706 607/27 |
| 2004/0263172 A1 | 12/2004 | Gray et al. | |
| 2005/0070787 A1 | 3/2005 | Zeijlemaker | |
| 2006/0167496 A1 * | 7/2006 | Nelson et al. | 607/2 |
| 2007/0021814 A1 * | 1/2007 | Inman et al. | 607/141 |
| 2007/0173910 A1 | 7/2007 | Armstrong | |
| 2008/0082146 A1 | 4/2008 | Gandhi et al. | |
| 2009/0138058 A1 * | 5/2009 | Cooke | A61N 1/3718 607/5 |
| 2009/0157146 A1 | 6/2009 | Linder et al. | |
| 2009/0210025 A1 * | 8/2009 | Ameri | 607/30 |
| 2009/0306735 A1 | 12/2009 | Lagercrantz et al. | |

FOREIGN PATENT DOCUMENTS

| | | |
|---|---|---|
| EP | 0670170 | 5/2002 |
| EP | 1493460 A1 * | 1/2005 |
| EP | 1493460 A1 | 5/2005 |
| WO | 2010/062978 A2 | 6/2010 |

OTHER PUBLICATIONS

Pinski et al., "Interference with Cardiac Pacing", (Cardiology Clinics, vol. 18, No. 1, Feb. 2000, pp. 219-239).

Fetter et al., "The Effects of Nuclear Magnetic Resonance Imagers on External and Implantable Pulse Generators" (PACE, vol. 7, pp. 720-727, Jul.-Aug. 1984).

\* cited by examiner

CONFIGURING OPERATING PARAMETERS OF A MEDICAL DEVICE BASED ON EXPOSURE TO A DISRUPTIVE ENERGY FIELD

TECHNICAL FIELD

The disclosure relates generally to implantable medical devices and, in particular, to the configuration of operating parameters of an implantable medical device (IMD) based on exposure to a disruptive energy field.

BACKGROUND

A wide variety of IMDs that deliver a therapy to and/or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in undesirable operation of the IMD. The IMD may be exposed to the disruptive energy field for any of a number of reasons. For example, one or more medical procedures may need to be performed on the patient within whom the IMD is implanted for purposes of diagnostics or therapy. For example, the patient may need to have a magnetic resonance imaging (MRI) scan, computed tomography (CT) scan, cardioversion, electrocautery, diathermy or other medical procedure that produces a magnetic field, electromagnetic field, electric field or other disruptive energy field.

The disruptive energy field may induce energy on one or more of the implantable leads coupled to the IMD or directly on one or more components of the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads or on the components of the IMD may result in inadvertent stimulation or heating of the tissue and/or nerve site adjacent to the electrodes of the leads or adjacent to the housing of the IMD. Such heating may compromise pacing and sensing thresholds at the site, which could result in reduced therapy efficacy.

SUMMARY

In general, this disclosure relates to adjusting one or more operating parameters of an implantable medical device (IMD) due to exposure of the IMD to a disruptive energy field. The disruptive energy field may, in one example, include magnetic and/or radio frequency (RF) fields generated by an MRI scanner. Although the techniques of this disclosure are described in the context of disruptive energy fields generated by an MRI scanner, the techniques may be used to control operation of the IMD within environments in which other types of disruptive energy fields of other sources are present.

The IMD may determine an effect of the disruptive energy field and adjust one or more operating parameters of the IMD based on at least the determined effect. The effect may be an effect at the tissue interface between an electrode and a tissue of a patient in which the IMD is implanted or an effect on operation of the IMD. In some instances, the IMD may determine an actual effect of the disruptive energy field, such as a temperature change, impedance change, pacing or sensing threshold change, MRI-induced interference on pacing or sensing or other effect. In other instances, the IMD may determine a predicted effect of the disruptive energy field based on one or more factors. For example, the IMD may predict a temperature change, impedance change, pacing or sensing threshold change or other effect based on a type of source of the disruptive energy field, a magnitude of the disruptive energy field, a duty cycle of the disruptive energy field, a frequency of the disruptive energy field, a type of lead of the IMD, or the like. In any case, the IMD adjusts one or more parameters based on at least the determined effect (actual or predicted).

In one example, this disclosure is directed to an implantable medical device comprising an effect determination module to determine an effect of a disruptive energy field and a parameter adjustment module to adjust at least one operating parameter of the implantable medical device based on at least the determined effect.

In another example, this disclosure is directed to a method comprising determining, with an implantable medical device, an effect of a disruptive energy field and adjusting at least one operating parameter of the implantable medical device based on at least the determined effect.

In a further example, this disclosure is directed to a device comprising means for determining an effect of a disruptive energy field and means for adjusting at least one operating parameter of the implantable medical device based on at least the determined effect.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
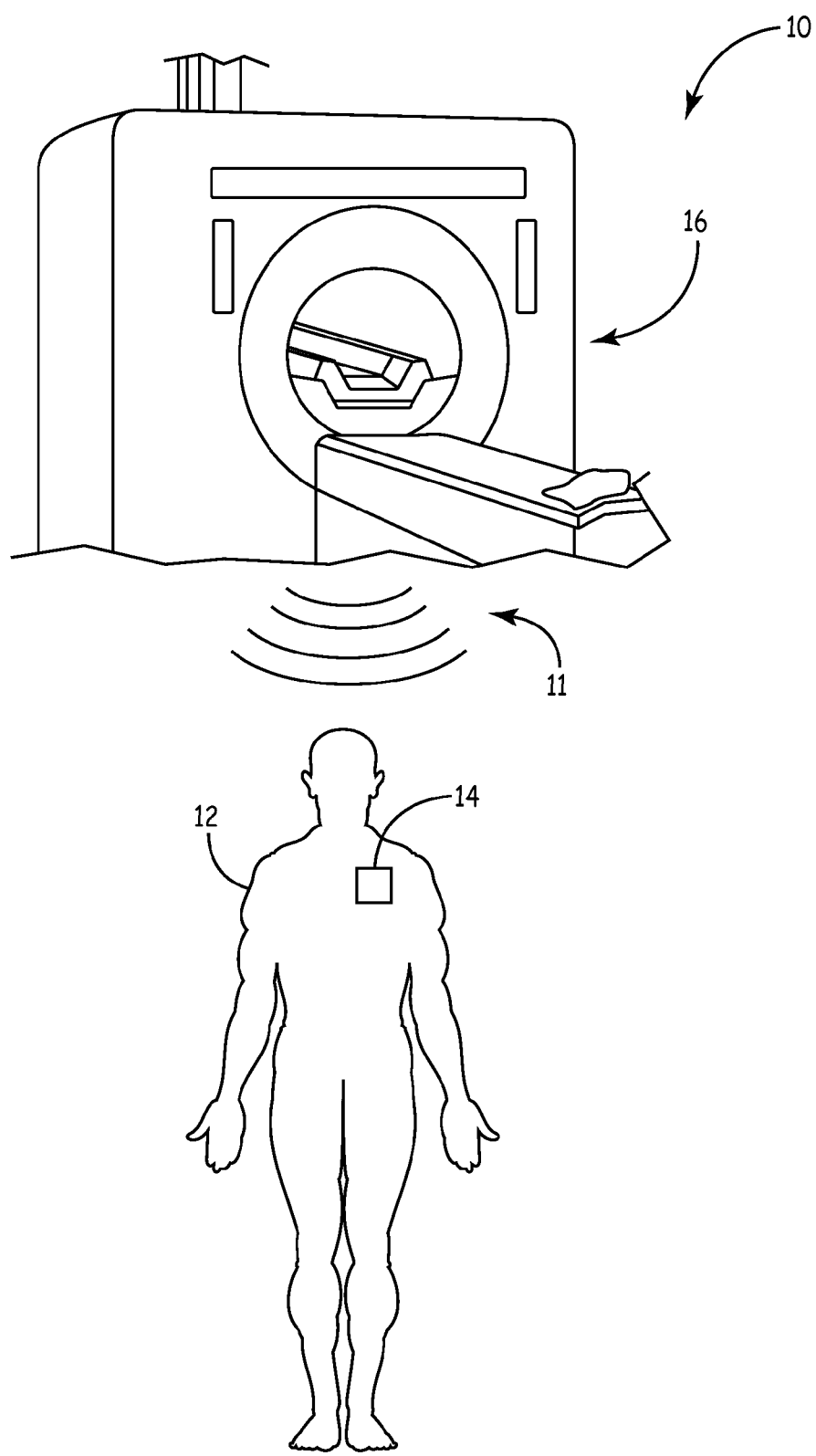
FIG. 1 is a conceptual diagram illustrating an environment in which an implantable medical device (IMD) is exposed to a disruptive energy field.

FIG. 1 is a conceptual diagram illustrating an environment 10 in which an implantable medical device (IMD) 14 is exposed to a disruptive energy field 11. IMD 14 is implanted within patient 12 to provide therapy to and/or to monitor a physiological condition of patient 12. The techniques of this disclosure, however, are not limited to devices implanted within patient 12. For example, the techniques may be used in conjunction with an external medical device that is adversely affected by disruptive energy field 11.

IMD 14 may be any of a variety of devices that provide therapy to patient 12, monitor a condition of patient 12, or both. For example, IMD 14 may be a device that provides electrical stimulation therapy via one or more implantable leads that include one or more electrodes (not shown in FIG. 1). In some instances, IMD 14 may be a device that provides electrical stimulation therapy in the form of cardiac rhythm management therapy to a heart of patient 12 via leads implanted within one or more atria and/or ventricles of the heart. In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarizatoin of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like. In some instances, IMD 14 may be used solely for monitoring a condition of patient 12. In other words, IMD 14 may not provide therapy to patient 12, but simply sense a physiological or biological condition of patient 12.

In yet other instances, IMD 14 may be a device that delivers a drug or therapeutic agent to patient 12, e.g., via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 10 includes an energy source or disruptive field source that generates disruptive energy field 11 to which IMD 14 is exposed. In the example illustrated in FIG. 1, the energy source or disruptive field source is an MRI scanner 16. Although the techniques of this disclosure are described with respect to disruptive energy field 11 generated by MRI scanner 16, the techniques may be used to control operation of IMD 14 within environments in which other types of disruptive energy fields are present. For example, IMD 14 may operate in accordance with the techniques of this disclosure in environments in which disruptive energy field 11 is generated by other sources, such as a CT scanner, X-ray machine, cardioversion device, external defibrillator, electrocautery device, diathermy device, ablation device, radiation therapy device, electrical therapy device, magnetic therapy device, RFID security gate, or any other environment with devices that radiate energy to produce magnetic, electromagnetic, electric fields or other disruptive energy fields.

MRI scanner 16 uses magnetic and radio frequency (RF) fields to produce images of body structures for diagnosing injuries, diseases and/or disorders. In particular, MRI scanner 16 generates a static magnetic field, gradient magnetic fields and/or RF fields. The static magnetic field is a non-varying magnetic field that is typically always present around MRI scanner 16 whether or not an MRI scan is in progress. Gradient magnetic fields are pulsed magnetic fields that are typically only present while the MRI scan is in progress. RF fields are pulsed RF fields that are also typically only present while the MRI scan is in progress. The magnitude, frequency or other characteristic of disruptive energy field 11 may vary based on the type of MRI scanner producing the field.

Some or all of the various types of fields produced by MRI scanner 16 may interfere with operation of IMD 14. In other words, one or more of the various types of fields produced by MRI scanner 16 may make up disruptive energy field 11. For example, the gradient magnetic or RF fields produced by MRI scanner 16 may induce energy on one or more of the implantable leads coupled to IMD 14. The induced energy on the leads or on the components of the IMD may be delivered to the tissue of patient 12 resulting heating of the tissue adjacent to electrodes of the leads or adjacent to the housing of the IMD. Such heating may compromise pacing and sensing thresholds at the site, which could result in reduced therapy efficacy. In some instances, IMD 14 may inappropriately detect the induced energy on the leads as physiological signals, which may in turn cause IMD 14 to deliver undesired therapy or withhold desired therapy. In other instances, the induced energy on the leads may result in IMD 14 not detecting physiological signals that are actually present, which may again result in IMD 14 delivering undesired therapy or withholding desired therapy.

To reduce the undesirable effects of disruptive energy field 11, IMD 14 may be capable of operating in accordance with settings that are less susceptible to undesirable operation during exposure to disruptive energy field 11, referred to herein as the "exposure mode" or "exposure operating mode." In the case of an exposure operating mode that specifically accounts for MRI scans, the mode may be referred to as an MR Conditional mode or an MR Safe mode. In some instances, IMD 14 may be configured from a normal operating mode (e.g., the current operating mode) to the exposure operating mode prior to being exposed or upon being exposed to disruptive energy field 11. For example, IMD 14 may be automatically configured into the exposure operating mode in response to detecting one or more conditions indicative of the presence of MRI scanner 16 or manually via an external programming device. In other instances, IMD 14 may be configured from the normal operating mode to the exposure operating mode after exposure to disruptive energy field 11 when it is determined that performance is compromised in environment 10.

In accordance with one aspect of this disclosure, IMD 14 may determine an effect of disruptive energy field 11 and adjust one or more operating parameters of IMD 14 based on at least the determined effect. The determined effect may be an effect at the tissue interface between an electrode and a tissue of patient 10 in which IMD 14 is implanted or an effect on operation of IMD 14, e.g., an effect on pacing or sensing integrity of IMD 14. In some instances, IMD 14 may determine an actual effect of disruptive energy field 11, such as a temperature change, impedance change, pacing or sensing threshold change, MRI-induced interference on pacing or sensing or the like. In other instances, IMD 14 may determine a predicted effect of disruptive energy field 11 based on one or more factors. For example, IMD 14 may predict a temperature change, impedance change, pacing or sensing threshold change or other effect based on a type of source of disruptive energy field 11, a magnitude of disruptive energy field 11, a duty cycle of disruptive energy field 11, a frequency of disruptive energy field 11, a type of lead of IMD 14, or the like. In any case, IMD 14 adjusts one or more parameters based on at least the determined effect (actual or predicted).

Figure 2:
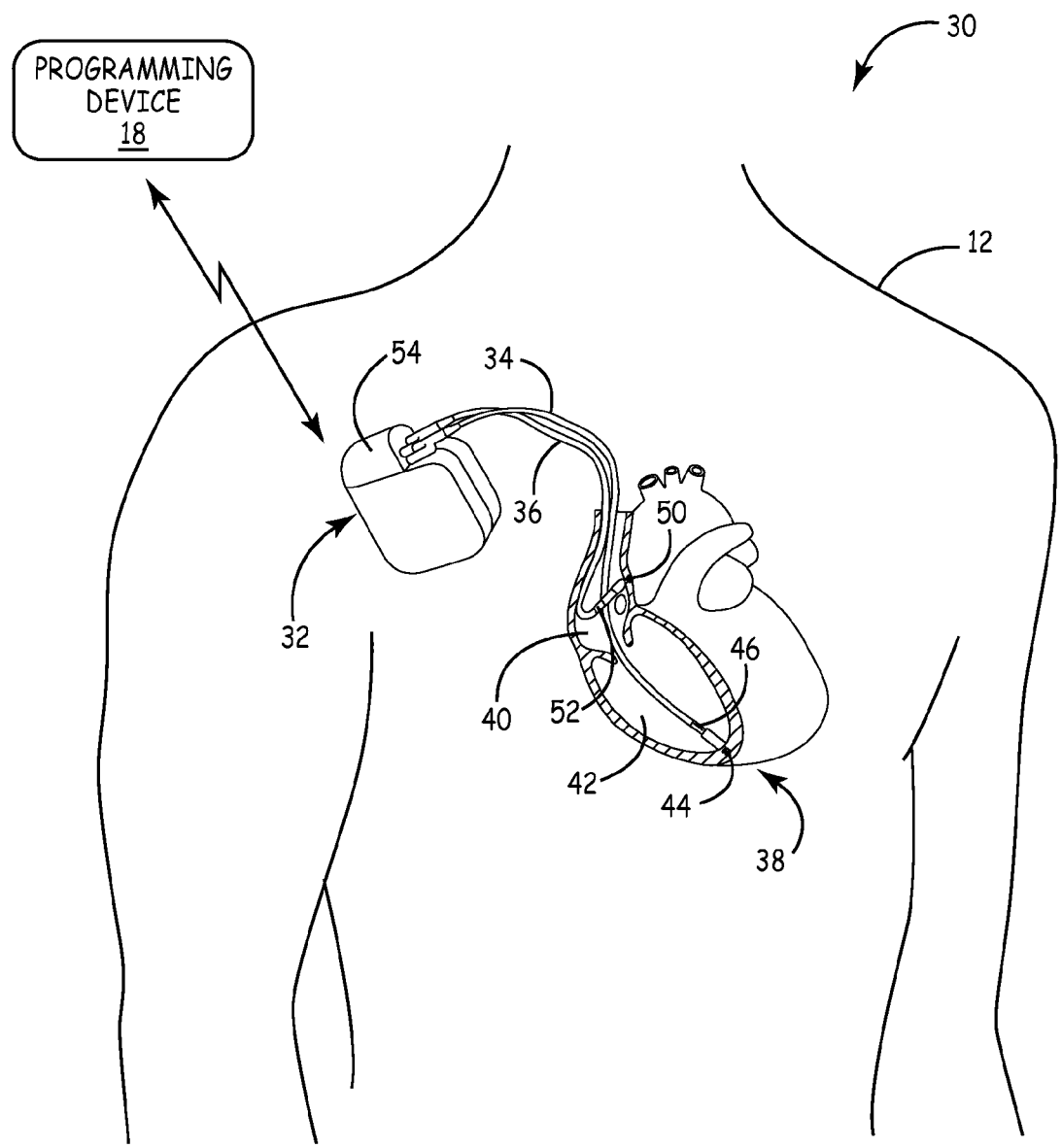
FIG. 2 is a conceptual diagram illustrating an example medical system that may be used to provide therapy to patient.

FIG. 2 is a conceptual diagram illustrating an example medical system 30 that may be used to provide therapy to patient 12. Medical system 30 includes an IMD 32 and leads 34 and 36 that extend from IMD 32. IMD 32 may, for example, correspond to IMD 14 of FIG. 1. IMD 32 wirelessly communicates with programming device 18.

In the example illustrated in FIG. 2, IMD 32 is an implantable cardiac device that senses electrical activity of a heart 38 of patient 12 and/or provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT). The combinations of cardiac therapies provided may be dependent on a condition of patient 12. In some instances, IMD 32 may provide no therapy to patient 12, but instead provide only sensing of electrical activity or other variable of heart 38, such as in the case of an implantable loop recorder.

In the illustrated example, lead 34 is a right ventricular (RV) lead that extends through one or more veins (not shown), the superior vena cava (not shown), and right atrium 40, and into right ventricle 42 of heart 38. Lead 34 includes electrodes 44 and 46 located along a distal end of lead 34. In the illustrated example, lead 36 is right atrial (RA) lead that extends through one or more veins and the superior vena cava, and into the right atrium 40 of heart 38. Lead 36 includes electrodes 50 and 52 located along a distal end of lead 36.

Electrodes 44 and 50 may take the form of extendable helix tip electrodes mounted retractably within an insulative electrode head (not shown) of respective leads 34 and 36. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated lead 34 or 36. Additionally, either or both of leads 34 and 36 may include more than two electrodes or only a single electrode.

Each of the electrodes 44, 46, 50 and 52 may be electrically coupled to a respective conductor within the body of its associated lead 34 and 36. The respective conductors may extend from the distal end of the lead to the proximal end of the lead and couple to circuitry of IMD 32. For example, leads 34 and 36 may be electrically coupled to a stimulation module, a sensing module, or other modules of IMD 32 via connector block 54. In some examples, proximal ends of leads 34 and 36 may include electrical contacts that electrically couple to respective electrical contacts within connector block 54. In addition, in some examples, leads 34 and 36 may be mechanically coupled to connector block 54 with the aid of set screws, connection pins or another suitable mechanical coupling mechanism.

When IMD 32 is capable of delivering electrical stimulation therapy, IMD 32 delivers the therapy (e.g., pacing pulses) to heart 38 via any combination of electrodes 44, 46, 50 and 52 to cause depolarization of cardiac tissue of heart 38. For example, IMD 32 may deliver bipolar pacing pulses to right atrium 40 via electrodes 50 and 52 of lead 36 and/or may deliver bipolar pacing pulses to right ventricle 42 via electrodes 44 and 46 of lead 34. In another example, IMD 32 may deliver unipolar pacing pulses to atrium 40 and ventricle 42 using a housing electrode (not shown) in conjunction with one of electrodes 44, 46, 50 and 52. The housing electrode may be formed integrally with an outer surface of the hermetically-sealed housing of IMD 32 or otherwise coupled to the housing. In some examples, the housing electrode is defined by an uninsulated portion of an outward facing portion of the housing of IMD 32.

Electrodes 44, 46, 50 and 52 may also sense electrical signals attendant to the depolarization and repolarization of heart 38. The electrical signals are conducted to IMD 32 via one or more conductors of respective leads 34 and 36. IMD 32 may use any combinations of the electrodes 44, 46, 50, 52 or the housing electrode for unipolar or bipolar sensing. As such, the configurations of electrodes used by IMD 32 for sensing and pacing may be unipolar or bipolar depending on the application. IMD 32 may analyze the sensed signals to monitor a rhythm of heart 38 or detect an arrhythmia of heart 38, e.g., tachycardia, bradycardia, fibrillation or the like. In some instances, IMD 32 provides pacing pulses (or other therapy) to heart 38 based on the cardiac signals sensed within heart 38. In other words, pacing may be responsive to the sensed events.

As described above, exposure of IMD 32 to a disruptive energy field 11 (FIG. 1) may result in undesirable operation. For example, gradient magnetic and RF fields produced by MRI scanner 16 (FIG. 1) may induce energy on one or more conductors of respective ones of implantable leads 34 and 36 or on the housing electrode. In some instances, the induced energy on conductors of leads 34 or 36 or on components of IMD 32 results in heating of the tissue adjacent to electrodes 44, 46, 50 and 52 or the housing of IMD 32. Such heating may compromise pacing and sensing thresholds at the tissue, which could result in reduced therapy efficacy. In other instances, IMD 32 may inappropriately detect the induced energy on the conductors of leads 34 or 36 as physiological signals, which may in turn cause IMD 32 to deliver undesired therapy or withhold desired therapy. In further instances, the induced energy on the conductors of leads 34 or 36 may result in IMD 32 not detecting physiological signals that are actually present, which may again result in IMD 32 delivering undesired therapy or withholding desired therapy.

Configuring IMD 32 into an exposure operating mode may reduce the undesirable effects that may be caused by exposure to disruptive energy field 11. As such, IMD 32 may be configured to operate in the exposure operating mode prior to or immediately subsequent to entering the environment 10 in which the disruptive energy field 11 is present, or prior to or immediately subsequent to the beginning of an MRI scan. Alternatively, IMD 14 may be configured from the normal operating mode to the exposure operating mode upon performance being compromised in environment 10, which may be determined based at least on the effect of disruptive energy field 11. For example, IMD 14 may be configured from the normal operating mode to the exposure operating mode upon detecting a change in a pacing or sensing threshold or upon detecting MRI-induced interference. Although the exposure operating mode may reduce the undesirable effects, it may not completely eliminate the undesirable effects. For example, the exposure operating mode may reduce heating at the tissue interface, but not completely eliminate it. In accordance with one aspect of this disclosure, IMD 32 determines an effect (actual or predicted) of disruptive energy field 11 and adjusts one or more operating parameters of IMD 32 based on at least the determined effect.

A user, such as a physician, technician, or other clinician, may interact with a programming device 18 to communicate with IMD 32. For example, the user may interact with programming device 18 to retrieve physiological information, diagnostic information, logs of delivered therapies, or an assessment of the performance or integrity of IMD 32 or other components of medical system 30, such as leads or a power source of IMD 32. For example, the user may use programming device 18 to retrieve information from IMD 32 regarding sensed physiological parameters of patient 12, such as electrical depolarization/repolarization signals from the heart (referred to as an "electrogram" or EGM), intracardiac or intravascular pressure, activity, posture, respiration or thoracic impedance.

The user may also interact with programming device 18 to program IMD 32, e.g., select values for operational parameters of IMD 32. For electrical stimulation therapies, for example, the user may interact with programming device 18 to program a therapy progression, select an electrode or combination of electrodes of leads 34 and 36 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes. The operating parameters may be parameters of a normal operating mode or an exposure operating mode.

The user may interact with programming device 18 to manually configure IMD 32 into or out of the exposure operating mode. The user may, for example, interact with programming device 18 to program IMD 32 into the exposure operating mode prior to patient 12 undergoing a medical procedure in which IMD 32 will be exposed to a disruptive energy field 11, e.g., before undergoing a MRI scan. The user may also reprogram IMD 32 from the exposure mode to a normal mode after the MRI scan is finished.

Programming device 18 may communicate with IMD 32 via wireless communication using any techniques known in the art. Examples of communication techniques may include, for example, magnetic telemetry, low frequency telemetry, RF telemetry, tissue conductance telemetry (in which the body is used as a conductor), or acoustic telemetry, but other techniques are also contemplated. In some instances, programming device 18 and IMD 32 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

Programming device 18 may be a dedicated hardware device with dedicated software for programming of IMD 32. Alternatively, programming device 18 may be an off-the-shelf computing device running an application that enables programming device 18 to program IMD 32. In some examples, programming device 18 may be a handheld computing device or a computer workstation. Programming device 18 may, in some instances, include a programming head that may be placed proximate to the patient's body near the implant site of IMD 32 in order to improve the quality or security of communication between IMD 32 and programming device 18. Programming device 18 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

The configuration of medical system 30 illustrated in FIG. 2 is merely an example. In other examples, medical system 30 may include more or fewer leads extending from IMD 32. For example, IMD 32 may be coupled to three leads, e.g., a third lead implanted within a left ventricle of heart 38. In another example, IMD 32 may be coupled to a single lead that is implanted within either an atrium or ventricle of heart 38. As such, IMD 32 may be used for single chamber or multi-chamber cardiac rhythm management therapy.

In addition to more or fewer leads, each of the leads may include more or fewer electrodes. In instances in which IMD 32 is used for therapy other than pacing, e.g., defibrillation or cardioversion, the leads may include elongated electrodes, which may, in some instances, take the form of a coil. IMD 32 may deliver defibrillation or cardioversion shocks to heart 38 via any combination of the elongated electrodes and housing electrode. As another example, medical system 30 may include leads with a plurality of ring electrodes, e.g., as used in some implantable neurostimulators.

In still other examples, a medical system may include epicardial leads and/or patch electrodes instead of or in addition to the transvenous leads 34 and 36 illustrated in FIG. 2. Further, IMD 32 need not be implanted within patient 12. In examples in which IMD 32 is not implanted in patient 12, IMD 32 may deliver electrical stimulation therapy to heart 38 via percutaneous leads that extend through the skin of patient 12 to a variety of positions within or outside of heart 38.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
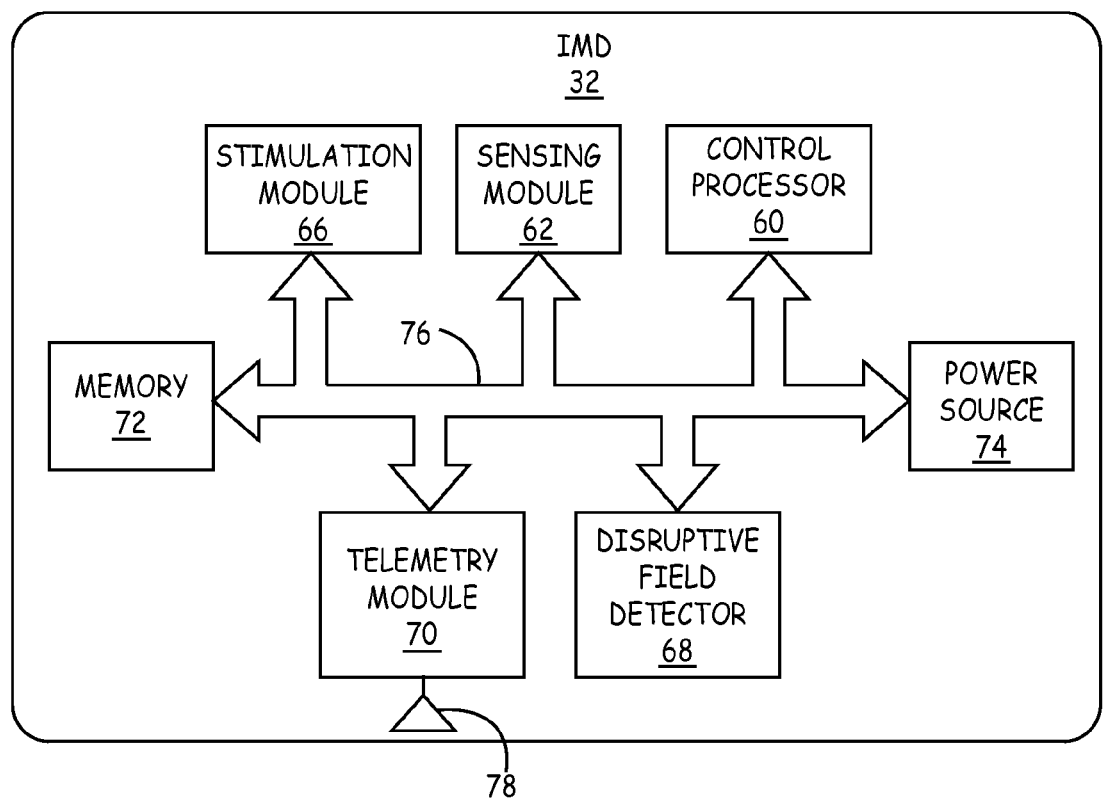
FIG. 3 is a functional block diagram of an example configuration of components of an IMD.

FIG. 3 is a functional block diagram of an example configuration of components of IMD 32. In the example illustrated by FIG. 3, IMD 32 includes a control processor 60, sensing module 62, stimulation module 66, disruptive field detector 68, telemetry module 70, memory 72 and power source 74, all of which are interconnected by a data bus 76. IMD 32 may include more or fewer components than illustrated in FIG. 3.

Processor 60 may determine an effect of disruptive energy field 11 and adjust one or more operating parameters of IMD 32 based on at least the determined effect. The effect may be an effect at a tissue interface, e.g., at an interface between an electrode of a lead and tissue adjacent to the electrode or an interface between a housing of IMD 32 and tissue adjacent to the housing. Instead, the effect may be an MRI-induced interference on pacing or sensing operations of IMD 32. In some instances, processor 60 may determine an actual effect of disruptive energy field 11. For example, IMD 32 may include a temperature sensor (not shown in FIG. 3) that measures a temperature change at a tissue interface. As another example, processor 60 may detect a sensing threshold change at a tissue interface. To do so, processor 60 may analyze the morphology (e.g., amplitude or shape), timing, or other characteristic of a sensed signal. As a further example, the effect may be an effect on IMD performance, such as, an effect on pacing integrity (e.g., detecting the lack of an evoked response to a pacing pulse due to a change in the pacing threshold or due to MRI-induced interference affecting the pacing pulse) or an effect on sensing integrity (e.g., detecting the occurrence of undersensing due to a change in the morphology of the EGM signal, or detecting the occurrence of oversensing due to MRI-induced interference).

In other instances, processor 60 may determine a predicted effect of disruptive energy field 11 based on one or more factors. The factors may include, but are not limited to, a characteristic of the exposure to disruptive energy field 11 (e.g., a type of source of disruptive energy field 11), a type of lead of IMD 32, or the like. Processor 60 may analyze one or more of these factors to predict the effect of disruptive energy field 11, e.g., predict a temperature change at the tissue interface, impedance change, pacing or sensing performance change, likelihood of oversensing or undersensing, or other effect.

In a further example, processor 60 may utilize various signal processing techniques to analyze an effect of disruptive energy field 11 on system performance and adjust one or more operating parameters of IMD 32 based on the determined effect. Processor 60 may, for instance, analyze a timing, morphology (e.g., amplitude or shape), amplitude, or other characteristic of a sensed signal to determine the effect of disruptive energy field 11 on system performance. Alternatively, processor 60 may analyze sensed signals to determine if an evoked response follows each delivered pacing pulse. In this manner, processor 60 may determine when disruptive energy field 11 compromises pacing or sensing integrity of IMD 32.

In any case, processor 60 adjusts one or more operating parameters based on at least the determined effect (actual or predicted). Processor 60 may, for example, adjust one or more pacing parameters (e.g., pacing amplitude, pacing pulse width, pacing rate or the like), sensing parameters (e.g., sensitivity of a sense amplifier, filter characteristics of the sense amplifier, sensing configuration), an operating mode (e.g., switch from a normal operating mode to an exposure operating mode) or the like, or a combination of such parameters. The operating parameters may be parameters that will be used during an exposure operating mode, during the normal operating mode upon no longer being exposed to disruptive energy field 11, or a combination thereof. Such adjustments may account for changes at the tissue interface caused by heating or changes in the integrity of IMD operation, thereby increasing the efficacy of the therapy.

Processor 60 may determine one or more characteristics of the exposure to disruptive energy field 11, including the presence of disruptive energy field 11, a magnitude of disruptive energy field 11, a duty cycle of disruptive energy field 11, a frequency of disruptive energy field 11, or other characteristic of the exposure. Processor 60 of IMD 32 may, for example, receive a signal from disruptive field detector 68 and analyze the signal from disruptive field detector 68 to detect a condition indicative of the presence of MRI scanner 16. In one example, disruptive field detector 68 is a magnetic field detector that provides an output that varies as a function of the magnitude of the magnetic field. Processor 60 may analyze the output of disruptive field detector 68 to determine whether the magnitude of the magnetic field exceeds a threshold or is within a particular threshold range, thus indicating the presence of MRI scanner 16. In another example, processor 60 may detect the condition indicative of the presence of MRI scanner 16 by analyzing a frequency of a detected RF field. To this end, magnetic field detector 68 may include an RF sensor comprising a stub, coil, or other structure that operates as an antenna to receive RF energy. In another example, a signal may be induced on antenna 78 by the pulsed RF fields generated by MRI scanner 16. In a further example, a signal may be induced on one or more conductors within leads 34 or 36 by the pulsed RF fields generated by MRI scanner 16.

In some instances, processor 60 may further determine a type of MRI scanner generating disruptive energy field 11. Processor 60 may determine the type of MRI scanner based on the signals used to detect the presence of MRI scanner 16 and/or based on one or more other signals. For example, processor 60 may determine the type of MRI scanner based on the signals from the magnetic field detector of disruptive field detector 68. Processor 60 may analyze these signals to determine whether the magnitude corresponds with a 1.5T MRI scanner or a 3.0T MRI scanner. In another example, processor 60 determines the type of MRI scanner based on a frequency of RF energy to determine the type of MRI scanner in addition to or instead of the magnitude of the magnetic field. Processor 60 may determine that the MRI scanner is a 1.5T scanner when the frequency of RF energy is approximately 64 MHz and determine that the MRI scanner is a 3.0T MRI scanner when the frequency of the RF energy is approximately 128 MHz.

To reduce the adverse effects of disruptive energy field 11, control processor 60 may be configured to operate IMD 32 in an exposure operating mode at some point during the exposure to disruptive energy field 11. The exposure operating mode is typically less susceptible to undesirable operation in disruptive energy field 11 than the normal operating mode. In other words, operating IMD 32 in the exposure mode may reduce some or all of the adverse effects that disruptive energy field 11 has on therapy delivery to patient 12. When operating in the exposure operating mode, control processor 60 is configured to operate with different functionality compared to the normal operating mode. Processor 60 may, in some instances, be configured to operate with reduced functionality. For example, processor 60 may not provide sensing, not deliver therapy, delivery only a subset of possible therapies, not log collected data or the like. In other instances, processor 60 may be operating with approximately the same functionality or even increased functionality in the exposure mode. For example, processor 60 may use a different sensor or algorithm to detect cardiac activity of the heart of patient 12, such as pressure sensor measurements rather than electrical activity of the heart.

Although the exposure operating mode may be less susceptible to some or all of the adverse effect of disruptive energy field 11, the exposure operating mode may not be the most efficacious or optimal operating mode. As such, processor 60 may configure IMD 32 to operate in the exposure operating mode after determining that performance of IMD 32, e.g., pacing or sensing performance, is being compromised by disruptive energy field 11. As will be described in further detail below, processor 60 may configure IMD 32 to operate in the exposure operating mode upon detecting a change in pacing or sensing thresholds or upon detecting MRI-induced interference. In this manner, processor 60 may adjust an operating mode based on a determined effect of disruptive energy field 11.

The operating parameters of the exposure operating mode may be stored within memory 72. In one example, processor 60 may receive the parameters of the exposure operating mode from a user via programming device 18. In other words, the exposure operating mode parameters may be manually configured by the user. In another example, at least a portion, and in some cases all, of the parameters of the exposure operating mode may be automatically determined. One example technique for automatically determining one or more parameters of the exposure operating mode is described in co-pending patent application Ser. No. 12/569,101 to Ellingson et al., entitled, "AUTOMATIC SELECTION OF PARAMETERS OF AN EXPOSURE MODE OF AN IMPLANTABLE MEDICAL DEVICE," which was filed on Sep. 29, 2009 and which is incorporated herein by reference in its entirety.

In some instances, processor 60 may select the same exposure operating mode regardless of a type of MRI scanner generating disruptive energy field 11. In other instances, processor 60 may select one of a plurality of exposure operating modes that corresponds to the type of MRI scanner. One such technique is described in detail in co-pending patent application Ser. No. 12/648,547, entitled, "CONFIGURING OPERATING PARAMETERS OF A MEDICAL DEVICE BASED ON A TYPE OF SOURCE OF A DISRUPTIVE ENERGY FIELD," which was filed on the same day as this disclosure and which is incorporated herein by reference in its entirety. For example, processor 60 may select operating parameters of a first exposure operating mode when the type of MRI scanner is a 1.5T MRI scanner and select operating parameters of a second exposure operating mode when the type of MRI scanner is a 3.0T MRI scanner. The selected exposure operating mode may include at least one operating parameter that is specifically tailored for exposure to a particular type of MRI scanner. For example, processor 60 may implement a filter to attenuate signals at a first frequency (e.g., 64 MHz) when operating in the exposure operating mode corresponding to a 1.5T MRI scanner and implement a filter to attenuate signals at a second frequency (e.g., 128 MHz) when operating in the exposure operating mode corresponding to a 3.0T MRI scanner. As another example, processor 60 may control stimulation module 66 to deliver therapy having a different pacing amplitude and/or pulse width based on the type of MRI scanner. Thus, the pacing amplitude and/or pulse width may be tailored for exposure to a specific type of MRI scanner.

Processor 60 may adjust one or more operating parameters of the selected exposure operating mode based on at least the determined effect of disruptive energy field 11. For example, processor 60 may adjust a pacing amplitude and/or pulse width used during the exposure operating mode based on the determined effect of disruptive energy field 11. As another example, processor 60 may adjust a sensitivity of sensing components used during the exposure operating mode based on the determined effect of disruptive energy field 11.

Upon no longer being exposed to disruptive energy field 11, control processor 60 may be configured to operate IMD 32 in the normal operating mode. In other words, processor 60 may disable the exposure operating mode. Processor 60 may automatically disable the exposure operating mode, e.g., in response to disruptive field detector 68 no longer detecting disruptive energy field 11 of MRI scanner 16, after a predetermined period of time (e.g., one hour), or other condition, or a combination of two or more conditions. In other instances, a user may manually disable the exposure operating mode of IMD 32, e.g., via interaction with programming device 18. Processor 60 may adjust one or more operating parameters to be used in the normal operating mode after exposure to disruptive energy field 11 based on at least the determined effect in accordance with the techniques of this disclosure.

The normal operating mode may correspond with the operating mode that a physician or other user feels provides a most efficacious or optimal therapy for patient 12. The normal operating mode may vary from patient to patient depending on the condition of patient 12 for which IMD 32 is providing therapy. In some instances, the normal operating mode may be adaptive in that the normal operating mode actually includes switching between more than one pacing mode based on the condition of the patient, such as described in U.S. Pat. No. 7,130,683 to Casavant et al., entitled, "PREFERRED ADI/R: A PERMANENT PACING MODE TO ELIMINATE VENTRICULAR PACING WHILE MAINTAINING BACKUP SUPPORT," which issued on Oct. 31, 2006 and which is incorporated herein by reference in its entirety.

The normal operating mode of IMD 32 may be one or more of any of a number of pacing modes, including DDD, VVI, DVI, VDD, AAI, DDI, DDDR, VVIR, DVIR, VDDR, AAIR, DDIR, VOO, AOO, DOO, ODO and other modes of single and dual-chamber pacing or sensing. For example, the normal operating mode may be an atrial based pacing mode, such as AAI or ADI pacing mode, if IMD 32 is providing therapy to a patient experiencing bradycardia. As another example, the normal operating mode may be a dual-chamber pacing mode, such as a DDD pacing mode, if IMD 32 is providing therapy to a patient with unreliable A-V conduction.

The exposure operating mode of IMD 32, on the other hand, may correspond with operating parameters that allow processor 60 to control IMD 32 in a manner in which the disruptive field energy does not affect or has a reduced effect on delivery of therapy. For example, the exposure mode may correspond with a pacing mode that does not provide sensing functionality. If patient 12 is pacing dependent, for example, the exposure mode of IMD 32 may correspond to an asynchronous pacing mode with no sensing, e.g., AOO, VOO or DOO. In another example, the exposure mode of IMD 32 may correspond to an asynchronous pacing mode that includes sensing, but has no mode of response to the pacing, e.g., such as a AAO, AVO, ADO, VVO, VAO, VDO, DDO, DAO or DVO pacing mode. In either of these cases, pacing is provided with no modification due to sensing. As such, the induced energy on the leads caused by disruptive energy field 11 does not result in undesirable operation of IMD 32.

In a further example, the exposure mode of IMD 32 may correspond to a sensing only mode, such as OAO, OVO or ODO, in which no pacing is provided. Such modes may only be used in cases in which patient 12 is not pacing dependent. Because there is no pacing in these pacing modes, such pacing modes may prevent IMD 32 from delivering undesirable stimulation or withholding desirable stimulation. Thus, when operating in the exposure operating mode, IMD 32 may provide no stimulation or sensing, provide stimulation but no sensing or provide sensing but no stimulation.

In the aforementioned operating modes, the abbreviations of which conform to the NBG Pacemaker Code, the first letter in the pacing mode indicates the chamber or chambers paced and may take on the letter "D" indicating dual-chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual-chamber (i.e., atrial and ventricle both paced), "V" indicating a ventricle is paced, "A" indicating an atrium is paced, or "O" indicating no chamber is paced. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

When IMD 32 is configured to generate and deliver therapy to heart 38, control processor 60 controls stimulation module 66 to deliver electrical stimulation therapy to heart 38 via one or more of electrodes 44, 46, 50, 52 and/or the housing electrode. Stimulation module 66 is electrically coupled to electrodes 44, 46, 50 and 52, e.g., via conductors of the respective lead 34 and 36, or, in the case of the housing electrode, via an electrical conductor disposed within the housing of IMD 32. Control processor 60 controls stimulation module 66 to generate and deliver electrical pacing pulses with the amplitudes, pulse widths, rates, electrode combinations or electrode polarities specified by a selected therapy program. For example, electrical stimulation module 66 may deliver bipolar pacing pulses via ring electrodes 46 and 52 and respective corresponding helical tip electrodes 44 and 50 of leads 34 and 36, respectively. Stimulation module 66 may deliver one or more of these types of stimulation in the form of other signals besides pulses or shocks, such as sine waves, square waves, or other substantially continuous signals. In addition to pacing pulses, stimulation module 66 may, in some instances, deliver other types of electrical therapy, such as defibrillation, cardioversion and/or cardiac resynchronization therapy.

Processor 60 may include a pacer timing and control module (not shown), which may be embodied as hardware, firmware, software, or any combination thereof. The pacer timing and control module may comprise a dedicated hardware circuit, such as an ASIC, separate from other components of control processor 60, or comprise a software module executed by a component of control processor 60, which may be a microprocessor or ASIC. In other instances, the pacer timing and control module may be part of stimulation module 66.

The pacer timing and control module may include programmable counters which control the basic time intervals associated with various single and dual-chamber pacing modes. Intervals defined by the pacer timing and control module within control processor 60 may include, for example, atrial and ventricular pacing escape intervals and refractory periods during which sensed atrial and ventricular events are ineffective to restart timing of the escape intervals. As another example, the pace timing and control module may define a blanking period, and provide signals to sensing module 62 to blank one or more channels, e.g., amplifiers, for a period during and after delivery of electrical stimulation to heart 38. The durations of these intervals may be determined by control processor 60 in response to parameters of the operating mode, which are stored in memory 72. The pacer timing and control module of control processor 60 may also determine the amplitude and pulse width of the cardiac pacing pulses.

During pacing, escape interval counters within the pacer timing and control module of control processor 60 may be reset upon sensing of R-waves and P-waves with detection channels of sensing module 62. Additionally, the value of the count present in the escape interval counters when reset by sensed R-waves and P-waves may be used by control processor 60 to measure the durations of R-R intervals, P-P intervals, P-R intervals and R-P intervals, which are measurements that may be stored in memory 72. Control processor 60 may analyze these various intervals to determine conditions of heart 38, such as to detect a tachyarrhythmia event. When IMD 32 is capable of providing defibrillation therapy, the R-R intervals may be used to increment a VF counter to control delivery of cardioversion or defibrillation shocks. For example, the VF counter may be incremented in response to detection of short R-R intervals, and possibly in response to other events such as R-R interval variance. The VF counter triggers delivery of a defibrillation shock when the counter reaches a number of intervals for detection (NID) threshold. Additionally, control processor 60 may begin an anti-tachyarrhythmia pacing regimen prior to delivery of the defibrillation shock.

Sensing module 62 is configured to receive signals from one or more sensors. In one example, sensing module 62 is configured to receive signals sensed by one or more of electrodes 44, 46, 50, 52 and the housing electrode. In this manner, electrodes 44, 46, 50, 52, and the housing electrode may operate as sense electrodes in addition to or instead of being used for delivering electrical stimulation therapy. In other instances, leads 34 and 36 may include one or more electrodes dedicated for sensing. In further examples, sensing module 62 is coupled to one or more sensors that are not included on leads 34 and 36, e.g., via a wired or wireless coupling. Such sensors may include, but are not limited to, temperature sensors, pressure sensors, accelerometers, flow sensors, blood chemistry sensors, activity sensors or other type of physiological sensor. Signals monitored by sensing module 62 may be stored in memory 72.

Sensing module 62 may include one or more detection channels, each of which may comprise a sense amplifier. The detection channels may be used to sense cardiac signals. Some detection channels may detect events, such as R- or P-waves, and provide indications of the occurrences of such events to processor 60. One or more other detection channels may provide the signals to an analog-to-digital converter, for processing or analysis by processor 60. In response to the signals from processor 60, a switch module (not shown) within sensing module 62 may couple selected electrodes to selected detection channels.

For example, sensing module 62 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 60 then uses that detection in measuring frequencies of the sensed events. Different narrow band channels of sensing module 62 may have distinct functions. For example, some various narrow band channels may be used to sense either atrial or ventricular events. Narrower band may include a narrower/tighter frequency range as well as steeper/higher order filter roll-off characteristics. IMD 32 could also use template matching from a period when there was no disruptive energy field and tune the filter characteristics to optimally reject the disruptive energy field.

In one example, at least one narrow band channel may include an R-wave amplifier that receives signals from the sensing configuration of electrodes 44 and 46, which are used for sensing and/or pacing in right ventricle 42 of heart 38. In addition, in some examples, a narrow band channel may include a P-wave amplifier that receives signals from electrodes 50 and 52, which are used for pacing and sensing in right atrium 40 of heart 38. The R-wave and P-wave amplifier may take the form of an automatic gain controlled amplifier that provides an adjustable sensing threshold. Other amplifiers may also be used. Furthermore, in some examples, one or more of the sensing channels of sensing module 62 may be selectively coupled to the housing electrode, with or instead of one or more of electrodes 44, 46, 50 or 52, e.g., for unipolar sensing of R-waves or P-waves.

In some examples, sensing module 62 includes a wide band channel which may comprise an amplifier with a relatively wider pass band than the R-wave or P-wave amplifiers. Signals from the sensing electrodes that are selected for coupling to this wide-band amplifier may be converted to multi-bit digital signals by an analog-to-digital converter provided by, for example, sensing module 62 or processor 60. In some examples, processor 60 may store the digitized versions of signals from the wide band channel as electrograms (EGMs) in memory 72. Processor 60 may employ digital signal analysis techniques to characterize the digitized signals from the wide band channel to, for example detect and classify the patient's heart rhythm. Processor 60 may detect and classify the patient's heart rhythm by employing any signal processing methodologies appropriate for the intended application or applications of IMD 32. Processor 60 may then control stimulation module 66 based on the signals sensed by sensing module 62.

As described above, the normal operating mode of IMD 32 may be susceptible to undesirable operation when IMD 32 is placed within environment 10 with disruptive energy field 11. In some instances, sensing module 62 inappropriately detects the induced energy on the leads as physiological signals (e.g., intrinsic cardiac events). In other words, IMD 32 senses a physiological signal when one is not actually present. At the very least, the detection of the induced energy caused by disruptive energy field 11 results in the stored data not accurately representing the actual function and condition of heart 38. Moreover, the detection of the induced energy caused by disruptive energy field 11 may in turn cause undesirable operation of IMD 32.

For example, when the current or normal operating mode is a pacing mode with inhibit response to sensing, processor 60 may not deliver (i.e., withhold) a desired pacing pulse in response to sensing the induced energy from disruptive energy field 11 as a physiological signal. For example, processor 60 may identify the induced energy as a ventricular event. This may result in control processor 60 resetting the ventricular escape interval counter, thereby inhibiting delivery of a desired pacing pulse. In other instances when the normal operating mode is a dual chamber pacing mode with inhibit and trigger response to sensing, processor 60 may also deliver an undesirable pacing pulse in addition to withholding a desired pacing pulse in response to sensing the induced energy from disruptive energy field 11 as a physiological signal. In particular, sensing the induced energy from the disruptive energy field as a physiological signal may inappropriately start an escape interval after which an undesired pacing pulse is delivered. This may result in dangerously fast heart rhythms and may lead to tachyarrhythmia or fibrillation.

In other instances, the induced energy on the leads may result in IMD 32 not sensing actual physiological signals that are present. Processor 60 may, for example, initiate a blanking period in response to the induced energy on the leads. During the blanking period, sensing module 62 may power down one or more sense amplifiers. As such, sensing module 62 will fail to detect any intrinsic physiological event that occurs during the blanking period. Failure to detect this actual physiological event may again result in IMD 32 delivering undesired therapy or withholding desired therapy.

In further instances, the induced energy on one or more of leads 34 and 36 or on one or more components of IMD 32 may result in heating of the tissue and/or nerve site adjacent to any of electrodes 44, 46, 50 and 52 of respective leads 34 and 36 or the housing of IMD 32. Such heating may compromise pacing and sensing thresholds at the tissue site, which could result in reduced therapy efficacy. To reduce the adverse effects of disruptive energy field 11, control processor 60 may be configured to operate IMD 32 in the exposure operating mode as described in detail herein.

Control processor 60 may include any one or more of a microprocessor, a controller, a DSP, ASIC, FPGA, or equivalent discrete or integrated circuitry, including analog circuitry, digital circuitry, or logic circuitry. The functions attributed to control processor 60 herein may be embodied as software, firmware, hardware or any combination thereof Memory 72 may include computer-readable instructions that, when executed by control processor 60 or other component of IMD 32, cause one or more components of IMD 32 to perform various functions attributed to those components in this disclosure. Memory 72 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

The various components of IMD 32 are coupled to power source 74, which may include a rechargeable or non-rechargeable battery. A non-rechargeable battery may be capable of holding a charge for several years, while a rechargeable battery may be inductively charged from an external device, e.g., on a daily or weekly basis. Power source 74 also may include power supply circuitry for providing regulated voltages and/or current levels to power the various components of IMD 32.

Under the control of processor 60, telemetry module 70 may receive downlink telemetry from and send uplink telemetry to programming device 18 with the aid of an antenna 78, which may be internal and/or external to IMD 32. Telemetry module 70 includes any suitable hardware, firmware, software or any combination thereof for communicating with another device, such as programming device 18. For example, telemetry module 70 may include appropriate modulation, demodulation, encoding, decoding, frequency conversion, filtering, and amplifier components for transmission and reception of data.

The various modules of IMD 32 may include one or more processors, such as one or more microprocessors, DSPs, ASICs, FPGAs, programmable logic circuitry, or the like, that may perform various functions and operations, such as those described herein.

Figure 4:
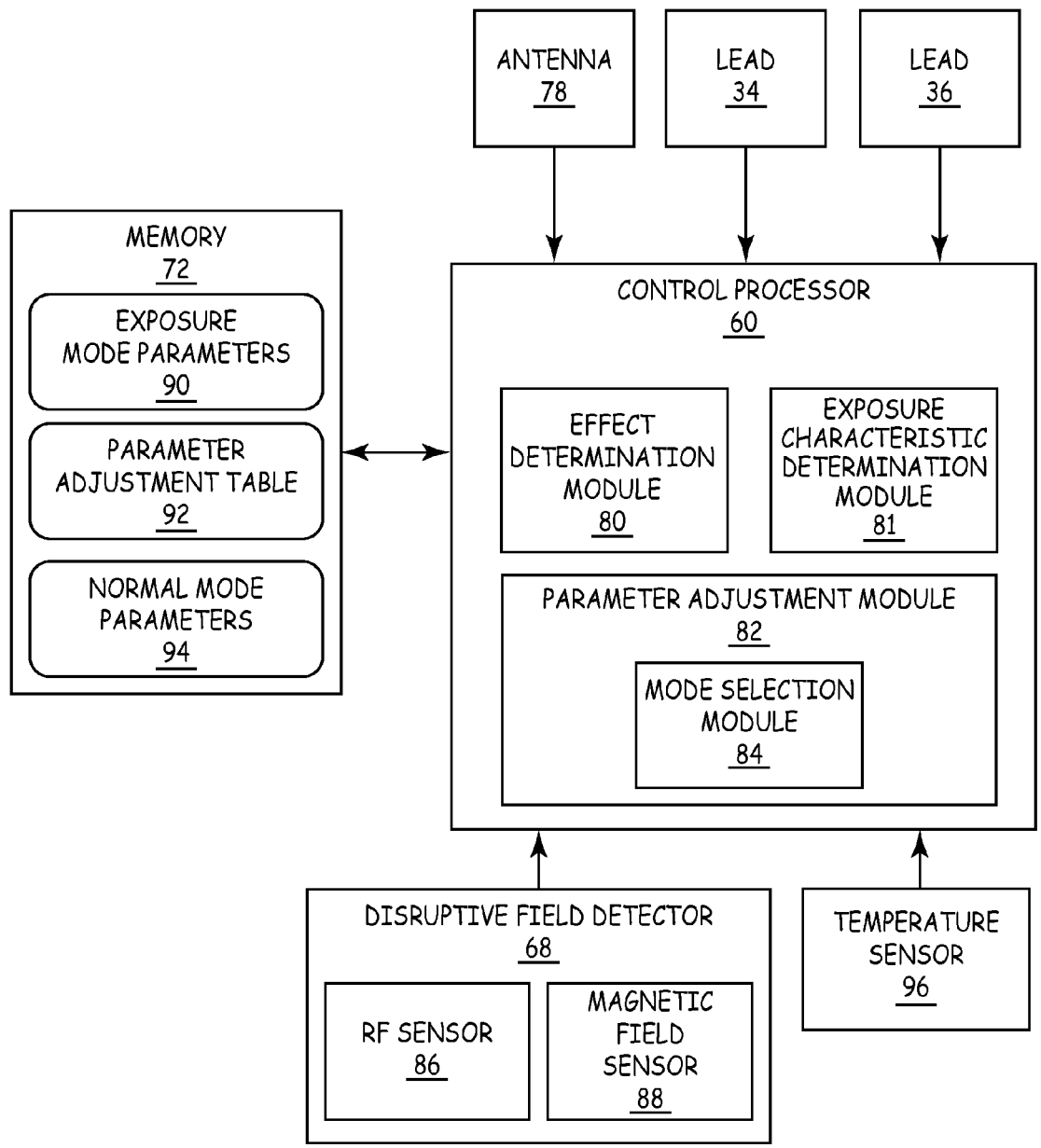
FIG. 4 is a functional block diagram illustrating some of the components of the IMD of FIG. 3 in further detail.

FIG. 4 is a functional block diagram illustrating control processor 60, disruptive field detector 68 and memory 72 in further detail. Processor 60 of FIG. 4 includes an effect determination module 80, an exposure characteristic determination module 81, a parameter adjustment module 82, and a mode selection module 84. Disruptive field detector 68 of FIG. 4 includes an RF sensor 86 and a magnetic field sensor 88. Control processor 60 and/or disruptive field detector 68 may include more or fewer components based on particular implementation of the techniques of this disclosure.

Effect determination module 80 determines an effect of disruptive energy field 11. For example, the effect is an effect at a tissue interface between an electrode and tissue adjacent to the electrode, e.g., an electrode of a lead or a housing electrode of IMD 32. As another example, the effect may be an effect on IMD performance, such as, an effect on pacing integrity or an effect on sensing integrity. In some instances, effect determination module 80 determines an actual effect of disruptive energy field 11. For example, effect determination module 80 may receive a signal from a temperature sensor 96 that measures a temperature change at a tissue interface. As another example, effect determination module 80 may determine a lead impedance change, a pacing threshold change or sensing threshold change at the tissue interface. In the case of a sensing threshold change, processor 60 may analyze timing, morphology (e.g., amplitude or shape) or other characteristic of a sensed signal to detect the effect. In the case of a pacing threshold change, processor 60 may sense to determine whether an evoked response follows each delivered pacing pulse and, if not, perform a capture management test to determine the pacing threshold. As a further example, processor 60 may detect an effect on pacing integrity by detecting the lack of an evoked response to a pacing pulse or due to MRI-induced interference affecting the pacing pulse itself. As yet another example, processor 60 may detect an effect on sensing integrity by detecting the occurrence of undersensing due to a change in the morphology of the EGM signal or detecting the occurrence of oversensing due to MRI-induced interference.

Effect determination module 80 may be triggered to determine the effect in response to one or more conditions. For example, effect determination module 80 may determine the effect in response to processor 60 determining that IMD 32 is no longer exposed to disruptive energy field 11. As another example, effect determination module 80 may be triggered to determine the effect based on a precursor effect. When the effect to be determined is a pacing threshold change, for instance, effect determination module 80 may perform a capture management test in response to failing to detect an evoked response or in response to detecting a lead impedance change. As a further example, effect determination module 80 may determine a pacing or sensing threshold in response to detecting a temperature change that exceeds a threshold temperature change. In another example, effect determination module 80 may determine a sensing threshold in response to detecting P-wave or R-wave amplitudes below and amplitude threshold.

In other instances, effect determination module 80 may determine a predicted effect of disruptive energy field 11 based on one or more factors. The factors may include, but are not limited to, a type of source of disruptive energy field 11 (e.g., type of MRI scanner), a magnitude of disruptive energy field 11, a duty cycle of disruptive energy field 11, a frequency of disruptive energy field 11, a type of lead of IMD 32, or the like. Effect determination module 80 may analyze one or more of these factors to predict the effect of disruptive energy field 11. In one example, effect determination module 80 may analyze the factors to predict the effect in response to one or more conditions, as described above.

In one aspect, effect determination module 80 may predict a temperature change at the tissue interface based on the one or more factors. The temperature change at the tissue interface may vary based on the type of MRI scanner and/or the type of MRI scanning sequence, since different MRI scanners and/or MRI scanning sequences utilize RF energy at different frequencies, amplitudes, and/or duty cycles. Additionally, the temperature change at the tissue interface may vary based on the type of lead of IMD 32. The amount of heating may be related to the dimensions of the electrode of the lead, a length of the lead, number of turns of the conductor, or the like. Effect determination module 80 may also predict additional effects of disruptive energy field 11 instead of or in addition to the temperature effect, including a predicted pacing threshold change or sensing threshold change, or an effect on IMD operation.

To this end, exposure characteristic determination module 81 may determine one or more characteristics of the exposure to disruptive energy field 11, including magnitudes of the magnetic or RF fields, frequencies of the magnetic or RF fields, duty cycles of the magnetic or RF fields or the like. Exposure characteristic module 81 may be coupled to one or more sensors, including RF sensor 86, magnetic field sensor 88, leads 34 or 36, antenna 78, or the like. Exposure characteristic determination module 81 may also include one or more timers to track the duty cycles of the magnetic or RF fields. Exposure characteristic determination module 81 may detect the presence of MRI scanner 16 and/or determine the type of MRI scanner based on the characteristics of disruptive energy field 11.

Whether effect determination module 80 determines an actual effect or a predicted effect, parameter adjustment module 82 may adjust one or more operating parameters based on at least the determined effect. Parameter adjustment module 82 may, for example, adjust one or more pacing parameters (e.g., pacing amplitude, pacing pulse width, pacing rate or the like) or sensing parameters (e.g., sensitivity of a sense amplifier). The adjusted pacing or sensing parameters may be for use during an exposure operating mode, during the normal operating mode upon no longer being exposed to disruptive energy field 11, or a combination thereof. Such adjustments may account for changes at the tissue interface caused by heating or other effect of disruptive energy field 11, thereby increasing the efficacy of the therapy.

Parameter adjustment module 82 may adjust the one or more operating parameters by selecting values for the operating parameters based on the predicted or actual effect. Parameter adjustment module 82 may, for example, retrieve the values for the one or more operating parameters from parameter adjustment table 92 stored in memory 72. Parameter adjustment table 92 may map the determined effect (e.g., temperature change, impedance change, a pacing threshold change or sensing threshold change) to corresponding values for operating parameters. Alternatively, parameter adjustment module 82 may run an algorithm that outputs an adjusted value for the operating parameter based on the determined effect.

In any case, parameter adjustment module 82 may also determine when to adjust the operating parameter based on the determined effect and/or based on a characteristic of the exposure to disruptive energy field 11. For example, parameter adjustment module 82 may compare the determined effect to a threshold value and adjust the one or more operating parameters based on the comparison. When the determined effect is a temperature change, for instance, parameter adjustment module 82 may adjust operating parameters when the temperature change exceeds a threshold temperature change. In this case, the determined temperature change is considered large enough to likely cause a change in pacing or sensing thresholds. When the temperature change does not exceed the threshold temperature change, parameter adjustment module 82 does not adjust the operating parameters. In this manner, parameter adjustment module 82 may use the determined effect to determine whether or not to adjust the operating parameters. Parameter adjustment module 82 may determine when to adjust the operating parameters based on other effects, such as pacing or sensing performance changes, lead impedance changes or the like.

Additionally, IMD 32 may generate an alert for the patient based on the comparison. For example, IMD 32 may generate an alert for the patient when an actual or predicted temperature change at the tissue interface exceeds a temperature change threshold. Similarly, IMD 32 may generate alerts based on other effects, including pacing or sensing performance changes, lead impedance changes or the like. The alert may be an audible alert (e.g., sound), a mechanical alert (e.g., stimulation or vibration), or other type of alert. IMD 32 may generate an alert for the patient and physician that is transmitted via telemetry module 70 to a patient monitoring device and/or a remote monitoring device, such as a CareLink® monitor, available from Medtronic, Inc. of Minneapolis, Minn. To this end, IMD 32 may include an alarm generation module (not shown in FIG. 4). IMD 32 may also send an alert (e.g., indicating high temperature at tissue interface or compromised operation) to an MRI operator or the MRI device such that the MRI scan may be stopped or altered to reduce the effects of disruptive energy field 11 on IMD 32.

As described above, control processor 60 may configure IMD 32 to operate in an exposure operating mode prior to or during exposure to disruptive energy field 11. The exposure operating mode is typically less susceptible to undesirable operation in disruptive energy field 11 than the normal operating mode. In other words, operating IMD 32 in the exposure mode may reduce some or all of the adverse effects that disruptive energy field 11 has on therapy delivery to patient 12.

In addition to or instead of adjusting the pacing or sensing parameters, parameter adjustment module 82 may adjust an operating mode of IMD 32 based on the determined effect. For example, mode selection module 84 may select an exposure operating mode upon detecting compromised IMD performance, such as, upon detecting an effect on pacing integrity (e.g., detecting the lack of an evoked response to a pacing pulse due to a change in the pacing threshold or due to MRI-induced interference affecting the pacing pulse) or upon detecting an effect on sensing integrity (e.g., detecting the occurrence of undersensing due to a change in the morphology, i.e., amplitude or shape, of the EGM signal, or detecting the occurrence of oversensing due to MRI-induced interference). In this manner, parameter adjustment module 82 may configure IMD 32 into the exposure operating mode when performance is compromised in environment 10. This allows IMD 32 to continue to operate in the normal operating mode, which is the more efficacious operating mode, until it is determined necessary to operate in the exposure operating mode. Depending on various other conditions, such as the type of MRI scanning sequence, the anatomical region of interest, the design of IMD 32, the programmed settings of IMD 32, or the like, IMD 32 may not necessarily need to operate in the exposure operating mode during the MRI scan.

Mode selection module 84 may select the exposure operating mode for IMD 32 based on one or more detected conditions. Mode selection module 84 may select the exposure operating mode for IMD 32 based on detection of a condition indicative of the presence of MRI scanner 16. As described above, exposure characteristic determination module 81 may detect the condition indicative of the presence of MRI scanner 16. Exposure characteristic determination module 81 may input signals from one or more of disruptive field detector 68, antenna 78, lead 34 or lead 36 and analyze the signals to detect the condition indicative of the presence of MRI scanner 16. In one example, exposure characteristic determination module 81 may detect the condition indicative of the presence of MRI scanner 16 based on input from magnetic field sensor 88, which may vary as a function of the magnitude of the magnetic field. Exposure characteristic determination module 81 may detect the condition indicative of the presence of MRI scanner 16 when the signal from magnetic field sensor 88 exceeds a threshold. Magnetic field sensor 88 may, for example, comprise a Hall effect sensor, magnetoresistive sensor or other magnetic field sensor. Exposure characteristic determination module 81 may, however, detect the presence of MRI scanner 16 using other signals detected by any one of or a combination of disruptive field detector 68, antenna 78, lead 34 or lead 36.

In some instances, mode selection module 84 selects an appropriate exposure operating mode tailored for the determined type of MRI scanner. In this case, exposure characteristic determination module 81 may determine the type of MRI scanner based on signals from one or more of disruptive field detector 68, antenna 78, lead 34 or lead 36. One such technique is described in detail in co-pending patent application Ser. No. 12/648,547, entitled, "CONFIGURING OPERATING PARAMETERS OF A MEDICAL DEVICE BASED ON A TYPE OF SOURCE OF A DISRUPTIVE ENERGY FIELD," which was filed on the same day as this disclosure and which is incorporated herein by reference in its entirety. In one example, exposure characteristic determination module 81 may determine the type of MRI scanner based on a magnitude of the magnetic field, e.g., determine that MRI scanner 16 is a 1.5T MRI scanner if the output of magnetic field sensor 88 is in a first range and determine MRI scanner 16 is a 3.0T MRI scanner when the output of magnetic field sensor 88 is in a second range.

In another example, exposure characteristic determination module 81 may determine the type of MRI scanner based on signals from one or more other sources in addition to or instead of the signals received from magnetic field sensor 88. For instance, exposure characteristic determination module 81 may determine a frequency of RF energy emitted subsequent to detecting the presence of MRI scanner 16 to determine the type of scanner, e.g., determine that the MRI scanner is a 1.5T scanner when the frequency of RF energy is approximately 64 MHz and determine that the MRI scanner is a 3.0T MRI scanner when the frequency of the RF energy is approximately 128 MHz.

To this end, exposure characteristic determination module 81 receives input from one or more components that receive the RF energy emitted by MRI scanner 16, such as RF sensor 86 of disruptive field detector 68. RF sensor 86 may include one or more coils, stubs, or other structure that operates as an antenna to receive RF energy. The structures or "antennas" of RF sensor 86 may be tuned to a frequency that is approximately equal to the frequency of the RF energy of the MRI scanner (e.g., 64 or 128 MHz in the case of a 1.5T or 3.0T MRI scanner). As another example, exposure characteristic determination module 81 may receive a signal from antenna 78 or one of leads 34 and 36 or a combination of RF sensor 86, antenna 38 and leads 34 or 36 and use the received signal(s) to determine whether RF energy of a particular frequency (e.g., RF energy of a frequency corresponding to a particular type of MRI scanner) is received. Although antenna 78 may not be tuned to the frequency utilized by MRI scanner 16, the pulsed RF signals of MRI scanner 16 may induce a signal on antenna 78. Likewise, conductors within leads 34 and 36 may act as an antenna when placed in environment 10. In other words, the pulsed RF signals of MRI scanner 16 may induce a signal on one of more of the conductors within leads 34 or 36. In any case, mode selection module 84 selects an exposure operating mode that corresponds to the determined type of MRI scanner.

Upon no longer being exposed to disruptive energy field 11, mode selection module 84 selects the normal operating mode parameters 94 and processor 60 configures IMD 32 to operate in the normal operating mode. In other words, processor 60 may disable the exposure operating mode. Processor 60 may automatically disable the exposure operating mode, e.g., in response to disruptive field detector 68 no longer detecting disruptive energy field 11 of MRI scanner 16, after a predetermined period of time (e.g., one hour), or other condition, or a combination of two or more conditions. In other instances, a user may manually disable the exposure operating mode of IMD 32, e.g., via interaction with programming device 18. As described above, processor 60 may adjust one or more operating parameters to be used in the normal operating mode after exposure to disruptive energy field 11 based on at least the determined effect in accordance with the techniques of this disclosure. Exposure operating mode parameters 90 and normal operating mode parameters 94 may be stored within memory 72.

Figure 5:
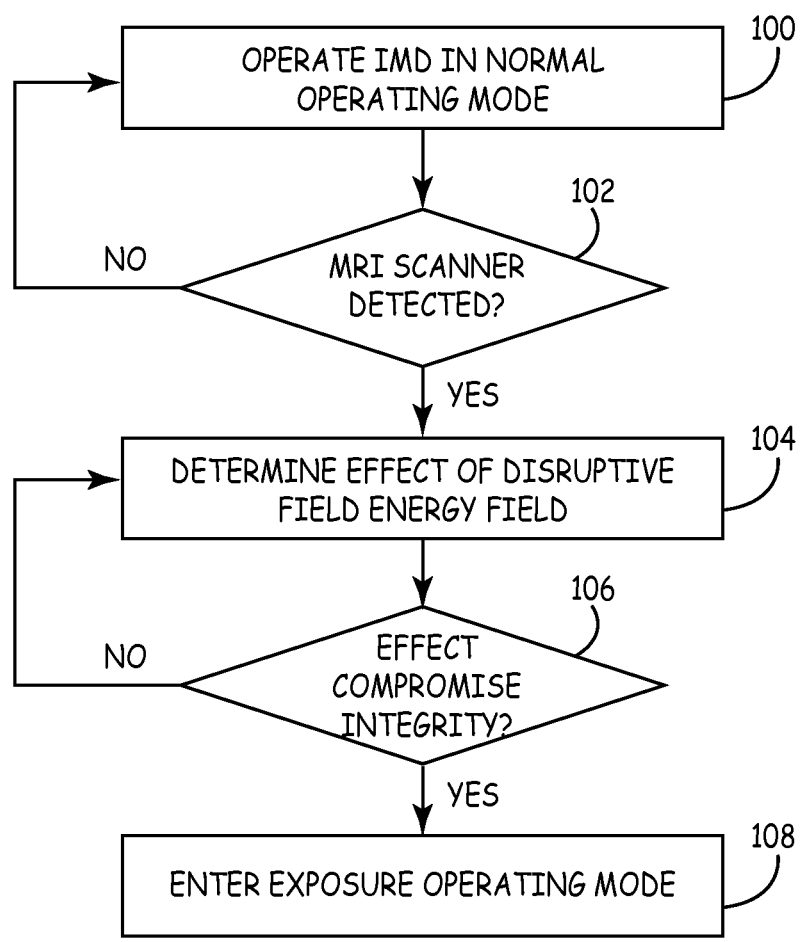
FIG. 5 is a flow diagram illustrating example operation of an IMD adjusting an operating mode based on a determined effect.

FIG. 5 is a flow diagram illustrating example operation of an IMD, such as IMD 32, adjusting operation based on at least one effect of a disruptive energy field. Processor 60 operates IMD 32 in a normal operating mode (100). As described above, the normal operating mode may correspond with the operating mode that a physician feels provides a most efficacious or optimal therapy for patient 12. The normal operating mode may vary from patient to patient depending on the condition of patient 12 for which IMD 32 is providing therapy.

Exposure characteristic determination module 81 monitors for the presence of MRI scanner 16 (102). Exposure characteristic determination module 81 may input signals from one or more of disruptive field detector 68, antenna 78, lead 34 or lead 36 and analyze the signals to detect a condition indicative of the presence of MRI scanner 16. When exposure characteristic determination module 81 does not detect the presence of MRI scanner 16 ("NO" branch of block 102), processor 60 continues to operate IMD in the normal operating mode.

When exposure characteristic determination module 81 detects the presence of MRI scanner 16 ("YES" branch of block 102), effect determination module 80 determines at least one effect of disruptive energy field 11 (104). In some instances, effect determination module 80 of processor 60 determines an actual effect of disruptive energy field 11. For example, effect determination module 80 may detect a temperature change, an impedance change, a pacing threshold change or sensing threshold change, or the occurrence of MRI-induced interference. In other instances, effect determination module 80 may determine a predicted effect of disruptive energy field 11. The factors may include, but are not limited to, a type of source of disruptive energy field 11 (e.g., type of MRI scanner), a magnitude of disruptive energy field 11, a duty cycle of disruptive energy field 11, a frequency of disruptive energy field 11, a type of lead of IMD 32, or the like.

Processor 60 determines whether the effect compromises the operational integrity of IMD 32 (106). When processor 60 determines that the effect does not compromise the operational integrity of IMD 32 ("NO" branch of block 106), processor 60 continues to monitor the effect of disruptive energy field 11. When processor 60 determines that the effect does compromise the operational integrity of IMD 32 ("YES" branch of block 106), processor 60 configures IMD 32 into an exposure operating mode (108). In some instances, processor 60 may determine a type of MRI scanner and select an exposure operating mode that is specifically tailored for the particular type of MRI scanner.

Figure 6:
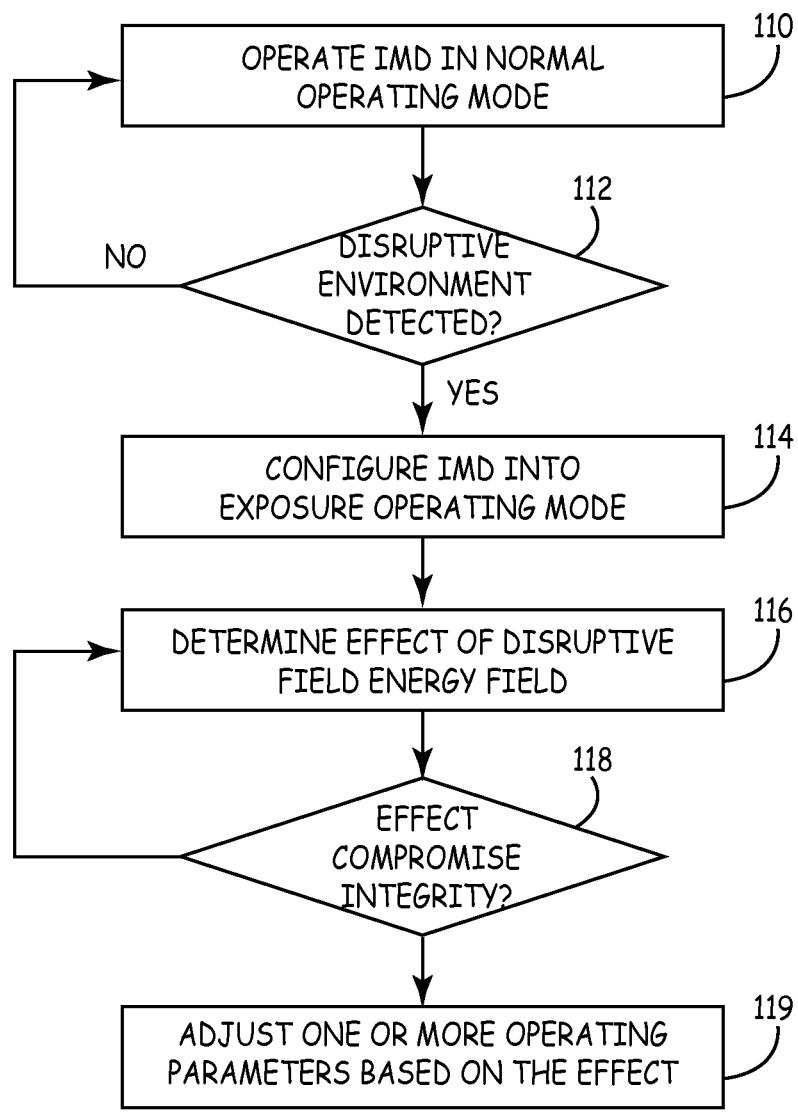
FIG. 6 is a flow diagram illustrating example operation of an IMD adjusting one or more operating parameters based on a determined effect.

FIG. 6 is a flow diagram illustrating example operation of an IMD, such as IMD 32, adjusting one or more operating parameters based on at least one effect of a disruptive energy field. Processor 60 operates IMD 32 in a normal operating mode (110). As described above, the normal operating mode may correspond with the operating mode that a physician feels provides a most efficacious or optimal therapy for patient 12 and may vary from patient to patient depending on the condition of patient 12 for which IMD 32 is providing therapy.

Exposure characteristic determination module 81 monitors for the presence of MRI scanner 16 (112). Exposure characteristic determination module 81 may input signals from one or more of disruptive field detector 68, antenna 78, lead 34 or lead 36 and analyze the signals to detect a condition indicative of the presence of MRI scanner 16. When exposure characteristic determination module 81 does not detect the presence of MRI scanner 16 ("NO" branch of block 112), processor 60 continues to operate IMD in the normal operating mode.

When exposure characteristic determination module 81 detects the presence of MRI scanner 16 ("YES" branch of block 112), processor 60 configures IMD 32 into an exposure operating mode (114). The exposure operating mode is typically less susceptible to undesirable operation in disruptive energy field 11 than the normal operating mode. In other words, operating IMD 32 in the exposure mode may reduce some or all of the adverse effects that disruptive energy field 11 has on therapy delivery to patient 12. In some instances, processor 60 may determine a type of MRI scanner and select an exposure operating mode that is specifically tailored for the particular type of MRI scanner.

Effect determination module 80 determines at least one effect of disruptive energy field 11 (116). In some instances, effect determination module 80 of processor 60 determines an actual effect of disruptive energy field 11. For example, effect determination module 80 may determine a temperature change, an impedance change, a pacing threshold change or sensing threshold change, or compromised IMD operation. In other instances, effect determination module 80 may determine a predicted effect of disruptive energy field 11. The factors may include, but are not limited to, a type of source of disruptive energy field 11 (e.g., type of MRI scanner), a magnitude of disruptive energy field 11, a duty cycle of disruptive energy field 11, a frequency of disruptive energy field 11, a type of lead of IMD 32, or the like.

Processor 60 determines whether the effect compromises the operational integrity of IMD 32 (118). When processor 60 determines that the effect does not compromise the operational integrity of IMD 32 ("NO" branch of block 118), processor 60 continues to monitor the effect of disruptive energy field 11. When processor 60 determines that the effect does compromise the operational integrity of IMD 32 ("YES" branch of block 118), parameter adjustment module 82 adjusts one or more operating parameters based on at least the determined effect (119). Parameter adjustment module 82 may, for example, adjust one or more pacing parameters (e.g., pacing amplitude, pacing pulse width, pacing rate or the like), sensing parameters (e.g., sensitivity of a sense amplifier), or the like, or a combination of such parameters. In some instances, the adjusted operating parameters may be parameters that will be used during the exposure operating mode. In other words, processor 60 may begin to utilize the adjusted operating parameters immediately. In other instances, the adjusted operating parameters may be parameters that will be used during the normal operating mode upon no longer being exposed to disruptive energy field 11 instead of or in addition to being used during the exposure operating mode. Such adjustments may account for changes at the tissue interface caused by heating or other effect, thereby increasing the efficacy of the therapy.

Figure 7:
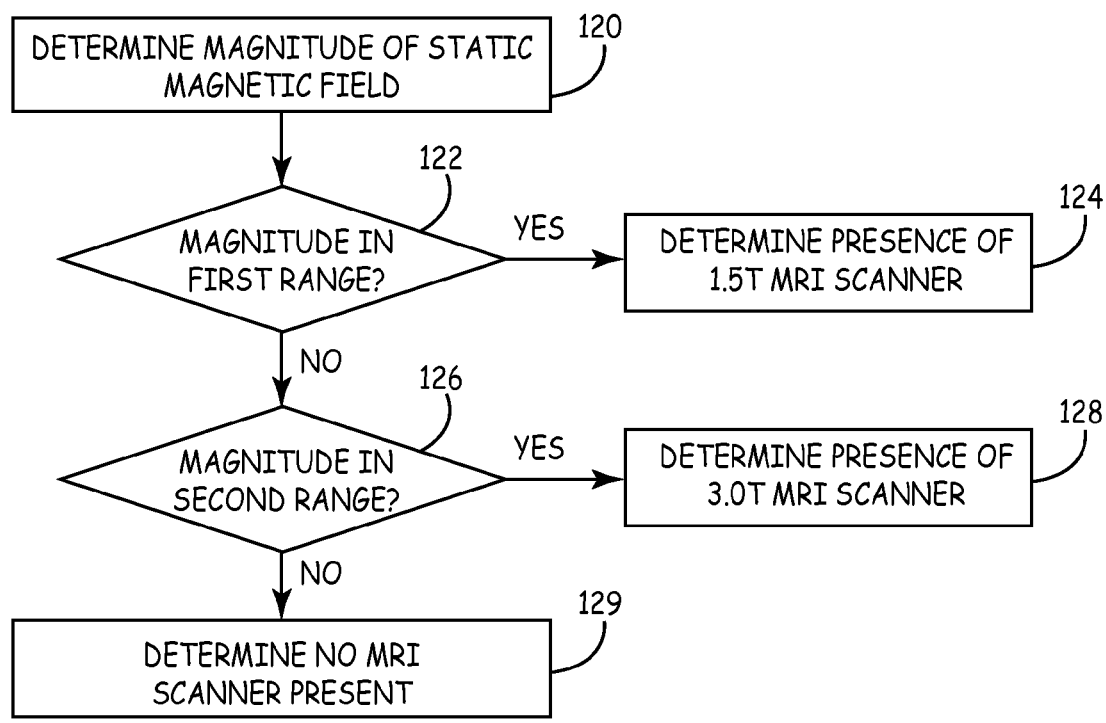
FIG. 7 is a flow diagram illustrating an example operation of an IMD determining a type of MRI scanner.

FIG. 7 is a flow diagram illustrating an example operation of an IMD, such as IMD 32 or IMD 14, determining the type of MRI scanner. Processor 60 of IMD 32 determines a magnitude of a static magnetic field to which IMD 32 is exposed (120). Processor 60 may, for example, obtain a signal from magnetic field sensor 88, which may vary as a function of the magnitude of the magnetic field, and analyze the signal to determine the magnitude of the magnetic field.

Processor 60 determines whether the magnitude of the static magnetic field is within a first range (122). The first range may correspond with a magnitude range of a first type of MRI scanner, e.g., a 1.5T MRI scanner. When processor 60 determines that the magnitude of the static magnetic field is within the first range, processor 60 determines the presence of a 1.5T MRI scanner (124).

When processor 60 determines that the magnitude of the static magnetic field is not within the first range, processor 60 determines whether the magnitude of the static magnetic field is within a second range (126). The second range may correspond with a magnitude range of a second type of MRI scanner, e.g., a 3.0T MRI scanner. When processor 60 determines that the magnitude of the static magnetic field is within the second range, processor 60 determines the presence of a 3.0T MRI scanner (128). If the magnitude of the magnetic field does not fall within either the first range or the second range, processor 60 determines that no MRI scanner is present (129).

Figure 8:
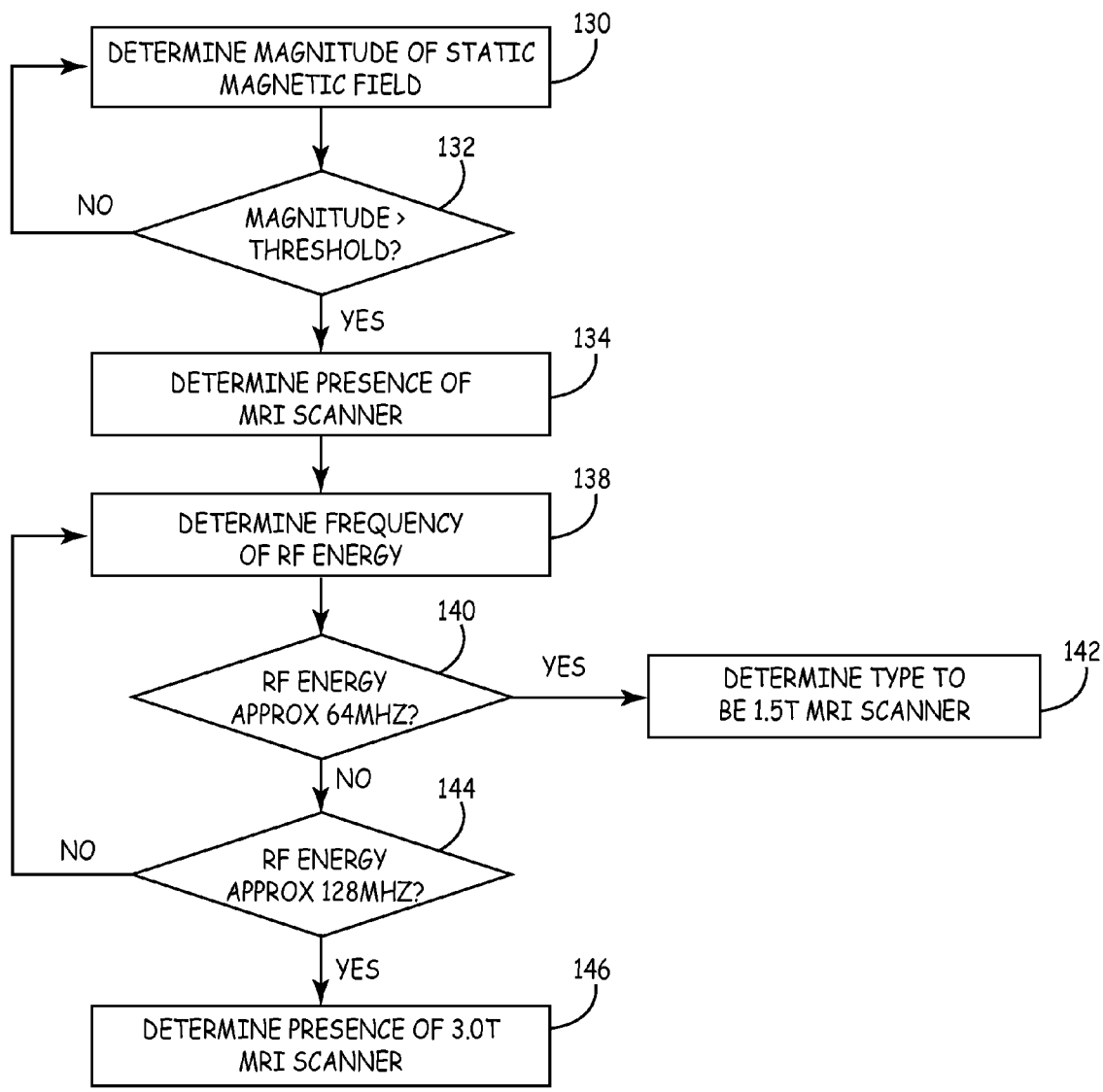
FIG. 8 is a flow diagram illustrating another example operation of an IMD determining a type of MRI scanner.

FIG. 8 is a flow diagram illustrating another example operation of an IMD, such as IMD 32, determining the type of MRI scanner. Processor 60 determines a magnitude of a static magnetic field to which IMD 32 is exposed (130). Processor 60 may, for example, obtain a signal from magnetic field sensor 88, which may vary as a function of the magnitude of the magnetic field, and analyze the signal to determine the magnitude of the magnetic field.

Processor 60 determines whether the magnitude of the static magnetic field is greater than a threshold (132). The threshold may be a value that is larger than the magnetic field required to enter the device into a magnet mode of operation (i.e., communication mode) and may encompass both the magnitude of the magnetic field generated by both 1.5T and 3.0T MRI scanners. When the magnitude of the magnetic field is not greater than the threshold, processor 60 continues to determine the magnitude of the magnetic field to which IMD 32 is exposed. When the magnitude of the magnetic field is greater than the threshold, processor 60 detects the presence of MRI scanner 16 (134).

Processor 60 determines a frequency of RF energy emitted subsequent to detecting the presence of MRI scanner 16 (138). To this end, processor 60 receives signals from one or more components that receive the RF energy emitted by MRI scanner 16, such as RF sensor 86, antenna 78, lead 34 or lead 36. Processor 60 determines whether the frequency of the RF energy is approximately equal to 64 MHZ (140). When processor 60 determines that the frequency is approximately equal to 64 MHz, processor 60 determines the presence of a 1.5T MRI scanner, i.e., determines the type of MRI scanner (142).

When processor 60 determines that the frequency is not approximately equal to 64 MHz, processor 60 determines whether the frequency of the RF energy is approximately equal to 128 MHZ (144). When processor 60 determines that the frequency is approximately equal to 128 MHz, processor 60 determines the presence of a 3.0T MRI scanner, i.e., determines the type of MRI scanner (146).

The techniques described in this disclosure, including those attributed to IMD 14 and/or 32, may be implemented, at least in part, in hardware, software, firmware or any combination thereof For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
a memory to store operating parameters of the implantable medical device;
a sensor that detects a disruptive energy field;
an effect determination module to determine an effect of the disruptive energy field on a tissue of a patient in which the implantable medical device is implanted or on operation of the implantable medical device after the sensor has detected the disruptive energy field;
a processor to determine whether the effect compromises the operational integrity of the implantable medical device; and
a parameter adjustment module to adjust at least one operating parameter of the implantable medical device to switch from a synchronous pacing mode to an asynchronous pacing mode when the processor determines that the effect does compromise the operational integrity of the implantable medical device and to not adjust the at least one operating parameter of the implantable medical device when the processor determines that the effect does not compromise the operational integrity of the implantable medical device, the parameter adjustment module adjusts the at least one operating parameter based on the determined effect.

2. The device of claim 1, wherein the effect determination module determines an actual effect of the disruptive energy field.

3. The device of claim 2, wherein the effect determination module determines one of a temperature change, an impedance change, a pacing threshold change, a sensing threshold change, or MRI-induced interference on pacing provided by the implantable medical device or MRI-induced interference on sensing signals received by the implantable medical device.

4. The device of claim 1, wherein the effect determination module determines a predicted effect of the disruptive energy field.

5. The device of claim 4,
further comprising an exposure characteristic determination module that determines one or more characteristics of the disruptive energy field,
wherein the effect determination module determines the predicted effect based on at least the one or more characteristics of the disruptive energy field.

6. The device of claim 5, wherein the exposure characteristic determination module determines one or more of a type of source of the disruptive energy field, a magnitude of the disruptive energy field, a frequency of the disruptive energy field, or a duty cycle of the disruptive energy field.

7. The device of claim 4, further comprising a lead coupled to the implantable medical device, wherein the effect determination module determines the predicted effect based on at least a lead type of the lead coupled to the implantable medical device.

8. The device of claim 1, wherein the parameter adjustment module compares the effect to a threshold and adjusts at least one operating parameter of the implantable medical device based on the comparison.

9. The device of claim 8, further comprising an alarm module to generate an alert based on the comparison.

10. The device of claim 1,
wherein the memory stores operating parameters of an exposure operating mode and operating parameters of a normal mode, the implantable medical device further comprising a mode selection module that configures the implantable medical device from the exposure operating mode to the normal operating mode upon no longer being exposed to the disruptive energy field,
wherein the parameter adjustment module adjusts at least one operating parameter of the normal operating mode to be used upon no longer being exposed to the disruptive energy field based on the determined effect.

11. The device of claim 1, wherein the memory stores operating parameters of an exposure operating mode that provides the asynchronous pacing mode and operating parameters of a normal mode that provides the synchronous pacing mode, the implantable medical device and the parameter adjustment module includes a mode selection module that configures the implantable medical device from the operating parameters of the normal operating mode to the operating parameters of the exposure operating mode based on at least the effect.

12. The device of claim 11, further comprising an exposure characteristic determination module that detects the presence of a source of disruptive energy field, wherein:
the effect determination module determines the effect in response to detecting the presence of the source; and
the mode selection module configures the implantable medical device from the normal operating mode to the exposure operating mode when the effect compromises operation of the implantable medical device.

13. The device of claim 1, wherein the operating parameters stored by the memory include at least one of a pacing amplitude parameter, a pacing rate or a pacing pulse width and wherein the at least one operating parameter being adjusted comprises the pacing amplitude, the pacing rate or the pacing pulse width.

14. The implantable medical device of claim 1, wherein the parameter adjustment module utilizes a table that maps the determined effect to the operating parameter to adjust the operating parameter.

15. The implantable medical device of claim 1, wherein the operating parameters stored by the memory include a pacing amplitude, a pacing rate, and a pacing pulse width and wherein the at least one operating parameter being adjusted comprises the pacing amplitude, the pacing rate, and the pacing pulse width.

16. A method comprising:
storing operating parameters of an implantable medical device in a memory;
sensing a disruptive energy field at the implantable medical device;
after sensing the disruptive energy field, then determining, with the implantable medical device, an effect of the disruptive energy field on a tissue of a patient in which the implantable medical device is implanted or on operation of the implantable medical device;

determining, with the implantable medical device, whether the effect compromises the operational integrity of the implantable medical device;

adjusting at least one operating parameter of the implantable medical device to change a pacing amplitude when the effect is determined to compromise the operational integrity of the implantable medical device, the adjusting of the at least one operating parameter being based on the determined effect; and maintaining the at least one operating parameter of the implantable medical device when the effect is determined to not compromise the operational integrity of the implantable medical device.

17. The method of claim 16, wherein determining the effect comprises determining an actual effect of the disruptive energy field.

18. The method of claim 17, wherein determining the actual effect of the disruptive energy field comprises measuring one of a temperature change, an impedance change, a pacing threshold change, a sensing threshold change, or an MRI-induced interference on pacing provided by the implantable medical device or MRI-induced interference on sensing signals received by the implantable medical device.

19. The method of claim 16, wherein determining the effect comprises determining a predicted effect of the disruptive energy field.

20. The method of claim 19, further comprising:
determining one or more characteristics of the disruptive energy field; and
determining the predicted effect based on at least the one or more characteristics of the disruptive energy field.

21. The method of claim 20, wherein determining the one or more characteristics of the disruptive energy field comprises determining one or more of a type of source of the disruptive energy field, a magnitude of the disruptive energy field, a frequency of the disruptive energy field, or a duty cycle of the disruptive energy field.

22. The method of claim 19,
further comprising determining, with the implantable medical device, a type of a lead coupled to the implantable medical device,
wherein determining the predicted effect comprises determining the predicted effect based on at least the type of lead.

23. The method of claim 16,
further comprising comparing the effect to a threshold; and
adjusting the at least one operating parameter of the implantable medical device based on the comparison.

24. The method of claim 23, further comprising generating an alert based on the comparison.

25. The method of claim 16, further comprising
storing operating parameters of an exposure operating mode and operating parameters of a normal operating mode in the memory; and
configuring the implantable medical device from an exposure operating mode to a normal operating mode upon no longer being exposed to the disruptive energy field,
wherein adjusting the at least one operating parameter of the implantable medical device includes adjusting at least one operating parameter of the normal operating mode to be used upon no longer being exposed to the disruptive energy field based on the determined effect.

26. The method of claim 16, wherein adjusting the at least one operating parameter comprises configuring the implantable medical device from a normal operating mode to an exposure operating mode based on at least the effect.

27. The method of claim 26, further comprising detecting the presence of a source of disruptive energy field, wherein:
determining the effect comprises determining the effect in response to detecting the presence of the source; and
configuring the implantable medical device comprises configuring the implantable medical device from the normal operating mode to the exposure operating mode when the effect compromises operation of the implantable medical device.

28. The method of claim 16, wherein
storing the operating parameters includes storing at least one of a pacing rate or a pacing pulse width and wherein the at least one operating parameter being adjusted comprises the pacing rate or the pacing pulse width.

29. An implantable medical device comprising:
means for storing operating parameters of the implantable medical device;
means for sensing a disruptive energy field;
means for determining an effect of the disruptive energy field on a tissue of a patient in which the implantable medical device is implanted or on operation of the implantable medical device after sensing the disruptive energy field;
means for determining, with the implantable medical device, whether the effect compromises the operational integrity of the implantable medical device; and
means for adjusting at least one operating parameter of the implantable medical device to change a pacing pulse width when the effect is determined to compromise the operational integrity of the implantable medical device, wherein the means for adjusting do not adjust the at least one operating parameter of the implantable medical device when the effect is determined to not compromise the operational integrity of the implantable medical device, the means for adjusting the at least one operating parameter basing the adjustment on the determined effect.

30. The device of claim 29, wherein the means for determining the effect determines an actual effect of the disruptive energy field.

31. The device of claim 30, wherein the means for determining the effect measures one of a temperature change, an impedance change, a pacing threshold change, a sensing threshold change, or an MRI-induced interference on pacing provided by the implantable medical device or MRI-induced interference on sensing signals received by the implantable medical device.

32. The device of claim 29, wherein the means for determining the effect determines a predicted effect of the disruptive energy field.

33. The device of claim 32,
further comprising means for determining one or more characteristics of the disruptive energy field,
wherein the means for determining the effect determine the predicted effect based on at least the one or more characteristics of the disruptive energy field.

34. The device of claim 33, wherein the one or more characteristics of the disruptive energy field include one or more of a type of source of the disruptive energy field, a magnitude of the disruptive energy field, a frequency of the disruptive energy field, or a duty cycle of the disruptive energy field.

35. The device of claim 29, wherein the means for storing stores operating parameters of an exposure operating mode and operating parameters of a normal operating mode, the device further comprising means for configuring the implantable medical device from the exposure operating mode to the normal operating mode upon no longer being exposed to the disruptive energy field, wherein the means for adjusting the at least one operating parameter adjusts at least one operating parameter of the normal operating mode to be used upon no longer being exposed to the disruptive energy field based on the determined effect.

36. The device of claim 29, wherein the means for adjusting the at least one operating parameter configures the implantable medical device from a normal operating mode to an exposure operating mode based on at least the effect.

37. The device of claim 36, further comprising means for detecting the presence of a source of disruptive energy field, wherein:

the means for determining the effect determine the effect in response to detecting the presence of the source; and the means for configuring the implantable medical device configure the implantable medical device from the normal operating mode to the exposure operating mode when the effect compromises operation of the implantable medical device.

38. The implantable medical device of claim 29, wherein the at least one operating parameter comprises at least one of a pacing amplitude, a pacing pulse rate, and a sensitivity of a sensing amplifier.

\* \* \* \* \*